United States Patent [19]
Perttu et al.

[11] Patent Number: 6,035,235
[45] Date of Patent: Mar. 7, 2000

[54] AMPLIFIED VOLTAGE OUTPUT SWITCHING NETWORK FOR A SELF-POWERED DEFIBRILLATOR

[75] Inventors: Joseph Perttu, Chanhassen; Dennis Brumwell, Bloomington, both of Minn.

[73] Assignee: Angeion Corp., Minneapolis, Minn.

[21] Appl. No.: 09/050,771

[22] Filed: Mar. 30, 1998

[51] Int. Cl.$^7$ .................................................. A61N 1/39
[52] U.S. Cl. ......................................................... 607/5
[58] Field of Search ...................................... 607/5

[56] References Cited

U.S. PATENT DOCUMENTS

| | | |
|---|---|---|
| 4,345,604 | 8/1982 | Renirie . |
| 4,800,883 | 1/1989 | Wionstrom . |
| 4,823,796 | 4/1989 | Benson . |
| 4,850,357 | 7/1989 | Bach, Jr. . |
| 4,902,901 | 2/1990 | Pernyeszi . |
| 4,998,531 | 3/1991 | Bocchi et al. . |
| 5,360,979 | 11/1994 | Joseph et al. . |
| 5,470,341 | 11/1995 | Kuehn et al. ................. 607/5 |
| 5,488,553 | 1/1996 | Renger . |
| 5,532,498 | 7/1996 | Umberger et al. . |
| 5,545,181 | 8/1996 | Jacobson et al. . |
| 5,591,212 | 1/1997 | Keimel . |
| 5,626,619 | 5/1997 | Jacobson et al. . |
| 5,645,572 | 7/1997 | Kroll et al. ................. 607/5 |
| 5,674,266 | 10/1997 | Stendahl . |
| 5,693,952 | 12/1997 | Cox . |
| 5,722,999 | 3/1998 | Snell . |

FOREIGN PATENT DOCUMENTS

WO 98/02209  1/1998  WIPO .

*Primary Examiner*—William E. Kamm
*Assistant Examiner*—Carl H. Layno
*Attorney, Agent, or Firm*—Brad Patterson

[57] ABSTRACT

An amplified, isolated output control circuit is provided for controlling the output switching network of a self-powered defibrillator that delivers a high voltage electrical countershock through a plurality of electrodes. The defibrillator comprises a low voltage battery system, a high voltage capacitor system, a high voltage transformer connected between the battery system and the capacitor system, and an output switching network, such as an H-bridge switching network, connected between the capacitor system and the plurality of electrodes. The defibrillator is controlled by control circuitry that manages the charging and discharging of the electrical countershock and is connected to the output control circuitry. Preferably, the output control circuitry includes an isolated power supply, at least one optoisolator device and at least one amplifier circuit that is powered by the isolated power supply and is connected between the optoisolator device and a switch of the output switching network. The output control circuitry provides for actual high side control of the output switching network by allowing the high side switches of the output switching network to be turned on and off after the low side switches of the output switching network. Preferably, the isolated power supply also provides a boosted output that powers the control circuitry at least during charging of the capacitor system to insure an adequate supply of power.

13 Claims, 7 Drawing Sheets

AMPLIFIED VOLTAGE OUTPUT SWITCHING NETWORK FOR A SELF-POWERED DEFIBRILLATOR

FIELD OF THE INVENTION

The present invention relates to self-powered medical devices for treating cardiac fibrillation, such as portable external defibrillators and implantable defibrillators, which deliver a high voltage electrical countershock to the heart. More particularly, the present invention pertains to an amplified high voltage output switching network for a self-powered defibrillator that includes an isolated supply for providing amplified power to the control circuitry of the output switching network of the defibrillator, particularly the high side output switches.

BACKGROUND OF THE INVENTION

Self-powered medical devices for treating cardiac fibrillation, such as portable external defibrillators and implantable cardioverter defibrillator (ICD) devices, are well known. These devices deliver a high voltage electrical countershock to the heart in an attempt to reset or restart normal cardiac rhythm. Typically, a set of high voltage capacitors in the device are charged via a transformer from a low voltage battery power source. The output of the high voltage capacitors is then discharged into at least two electrodes to create the high voltage electrical countershock. Preferably, the output of the high voltage capacitors is routed through a high voltage output switching network known as an H-bridge in order to create a truncated biphasic waveform. The H-bridge switching network creates the biphasic waveform by using at least four high voltage electronic switches connected between the capacitors and the electrodes and arranged in an H-configuration to switch the polarity of the output midway through the discharge of the capacitors. Examples of H-bridge switching networks for implantable defibrillators are shown in U.S. Pat. Nos. 4,800,883, 4,850,357, 4,998,531 and 5,083,562.

To date, the implementation of the H-bridge in a self-powered defibrillator has been accomplished using at least four high powered electronic switches, with the switches on the bottom or low voltage pole of the H-bridge configuration referred to as the low side switches and the switches on the top or high voltage pole of the H-bridge configuration are referred to as the high side switches. The H-bridge configuration is known for its ability to efficiently drive a load in two different directions from a DC voltage source. In a first phase, a first high side switch connects the high voltage pole (+HV) of the DC voltage source (the charged high voltage capacitors) to a first side of the load and a second low side switch connects a second side of the load to the low voltage pole (−HV) of the DC voltage source. To terminate the first phase, the second low side switch is turned off, thereby stopping current flow through both the first and second switches, after which the high side switch may be turned off. The second phase is initiated by a third high side switch that connects the high voltage pole (+HV) to the second side of the load and a fourth low side switch that connects the low voltage pole (−HV) to the first side of the load. The second phase is terminated similar to the first phase by turning off the fourth low side switch, after which current has stopped flowing through the load and the third high side switch may be turned off. For a more detailed description of the operation of the H-bridge circuitry of a defibrillator, reference is made to Bach, S. et al., "High Power Circuitry," *Implantable Cardioverter Defibrillator Therapy: The Engineering Clinical Interface*, Chpt. 13, pp. 257–273, eds. Kroll, M. and Lehmann, M. (1996).

Because the switches in an H-bridge network must be turned on and off quickly and safely, existing designs for an H-bridge in a self-powered defibrillator use the two low side switches to control the operation of the H-bridge switch as just described. Originally, the low side switches were used for control of the H-bridge because the high side switches typically were silicon controlled rectifier (SCR) switches which cannot be turned off quickly or easily. As high power switches other than SCR switches (e.g., IGBT and MOSFET switches) have been used for the high side switches in an H-bridge a different problem known as hot switching has continued the reliance on the low side switches for controlling the operation of the H-bridge. Hot switching occurs when a switch turns on or off while passing current. The problem is that the switch must dissipate energy during hot switching. This dissipated energy is usually in the form of heat and is the product of the current through the switch and the voltage across the switch integrated over the transition time of the hot switching. If the voltages across the switch are large and the transition time is too long, it is possible for the dissipated heat to damage the switch. Because the low side switches are easier and quicker to control, the problems associated with hot switching are more manageable and the use of the low side switches to control the operation of the H-bridge switch has continued.

Even though the low side switches are used to control the H-bridge circuitry, the control voltages of 12–18 volts for the low side switches are still higher than the typically battery voltages of 3–9 volts. As a result, existing defibrillators typically include a voltage multiplier that increases the battery voltage to the voltage necessary to operate the low side switches. It has been found, however, that during periods of high current draw on the battery (such as when the battery is charging the capacitors), the ability of these voltage multiplier circuits to maintain the necessary voltages across the low side switches to prevent an unintended discharge can be compromised. U.S. Pat. No. 5,372,605 describes a dual battery system for an implantable defibrillator in which a booster circuit is incorporated into the design of the power circuitry of the device to insure that there is adequate voltage for controlling the low side switches, as well as other critical circuitry in the device, during periods of high current drain from the battery.

Because of the high voltages and high currents which are involved, it is also necessary to isolate the control circuitry for the H-bridge from the remaining circuitry in the device. Two alternative techniques have been used to accomplish this isolation. Either the high voltage capacitors and the H-bridge switching networks, including its control circuitry, can be completely isolated from the rest of the circuitry, or the negative pole of the high voltage capacitors can be connected to a common negative ground with the rest of the circuitry, thereby requiring only that the high side control signals for the H-bridge be isolated. Most of the H-bridge designs described above use the common negative ground technique and use some kind of pulse transformer or RF carrier with rectification to achieve the necessary high side isolation. U.S. Pat. No. 5,545,181 describes the other technique for isolating the H-bridge output switching network in an implantable defibrillator. In this patent, the low side of the H-bridge is referenced to a supply voltage which is negative with respect to the pacing and sensing ground for the remaining circuitry of the device and which is connected to the positive side of the low voltage battery for the device.

Other improvements have been made to the operation of the control circuitry for the H-bridge output switching network. In U.S. Pat. No. 5,178,140, capacitive coupling is taught for isolating the control circuitry for the H-bridge and includes a common mode switch for rejecting noise. In U.S. Pat. No. 5,470,341, the control circuitry for the H-bridge includes circuitry to inhibit high voltage transient noise signals that may be generated during switching of the H-bridge circuitry so as to prevent inadvertent retriggering of the control circuitry. In U.S. Pat. No. 5,534,814, a high impedance gate driver circuit is utilized as part of the control circuitry in order to minimize the amount of base current needed to drive the IGBT high power switch which forms the H-bridge switching network in this patent.

In U.S. Pat. No. 4,823,796, a pair of optoisolators are used for isolation of a voltage detection circuit and an energy selection circuit for the output switching network of a self-powered external defibrillator. This patent otherwise uses conventional designs for isolating the high voltage output switching network from the remaining circuitry of the device and for controlling the switching operation of the output switching network.

In U.S. Pat. No. 5,626,619, an optically isolated shock control circuit is described. In this patent, several alternate embodiments of a high side and low side control circuits for the H-bridge are presented in which the control signal is transmitted by an optical phototransistors or photodiodes. This patent specifically describes how the optically isolated control circuit can be implemented with N-channel IGBT or MOSFET switches, instead of the conventional SCR switches. While the invention described in this patent represents a significant advance from previous isolated control circuits due to the use of the phototransistor as the isolation mechanism and the use of N-channel switches, the practical embodiment of the invention still relies on low side control of the H-bridge.

In U.S. Pat. No. 5,674,266, a diode isolated shock delivered circuit is described for a self-powered external defibrillation. In this patent, a four diode bridge having an input node and output node is used to isolate the H-bridge circuitry from the patient. The control circuitry for this design is driven by a conventional gate drive circuit that is controlled by an isolated pulse control signal.

In U.S. Pat. No. 5,693,952, both a switch-on optoisolator and a switch-off optoisolator are used as isolation and control for the H-bridge circuitry. In one embodiment, the performance of the switch-on function is enhanced by using a first optoisolator to charge a small capacitor and then using a second optoisolator to discharge that capacitor to operate the high voltage switch in the H-bridge circuit.

U.S Pat. Nos. 4,902,901, 5,360,979 and 5,532,498 describe various control circuitry for optically controlled solid state switches that have improved switching performance. In each of these patents, isolation and control is accomplished using a photo-diode array as the current source for controlling the operation of the solid state switches. However, none of these circuits are specific to the requirements of the H-bridge circuitry within a self-powered defibrillator.

While the existing designs for the H-bridge and power circuitry for self-powered defibrillators are adequate, it would be desirable to provide improvements which could increase the performance efficiency of the defibrillator and which could allow for more flexibility in the operation of the defibrillator.

SUMMARY OF THE INVENTION

The present invention provides an amplified, isolated output control circuit for controlling the output switching network of a self-powered defibrillator that delivers a high voltage electrical countershock through a plurality of electrodes. The self-powered defibrillator comprises a low voltage battery system, a high voltage capacitor system, a high voltage transformer connected between the battery system and the capacitor system, and an output switching network, such as an H-bridge switching network, connected between the capacitor system and the plurality of electrodes. The defibrillator is controlled by control circuitry that manages the charging and discharging of the electrical countershock and is connected to the output control circuitry. Preferably, the output control circuitry includes an isolated power supply, at least one optoisolator device and at least one amplifier circuit that is powered by the isolated power supply and is connected between the optoisolator device and a switch of the output switching network.

The output switching circuitry includes at least two low side switches operably connected to a ground side of a secondary side of the transformer and at least two high side switches operably connected to a high voltage side of the secondary side of the transformer, which together form a conventional H-bridge switching network for delivering a biphasic waveform. Preferably, the high side switches are N-channel high power switches, such as an IGBT or N-channel MOSFET, and the output control circuitry provides for actual high side control of the output switching network by allowing the high side switches of the output switching network to be turned on and off after the low side switches of the output switching network.In a preferred embodiment, the isolated power supply also provides a boosted output that powers the control circuitry at least during charging of the capacitor system to insure an adequate supply of power during this time of increased drain on the battery.

The amplifier circuit in the isolated output control circuitry of the present invention provides for an increased gain that is applied to the gate of high side switches to significantly decrease the transition time for switching the high side switches on and off. Coupled with the beta gain of the phototransistor, the amplifier circuit provides for at least a double beta gain increase in the instantaneous current available to the gate of the N-channel high power high side switch that allows the gate to emitter voltage to be greater than the turn on voltage of this switch. In addition, a double beta gain is provided as part of an amplified turn-off portion of the amplifier circuit to increase the speed at which the N-channel high power high side switch can be turned off

DESCRIPTION OF THE PREFERRED EMBODIMENT

Figure 1:
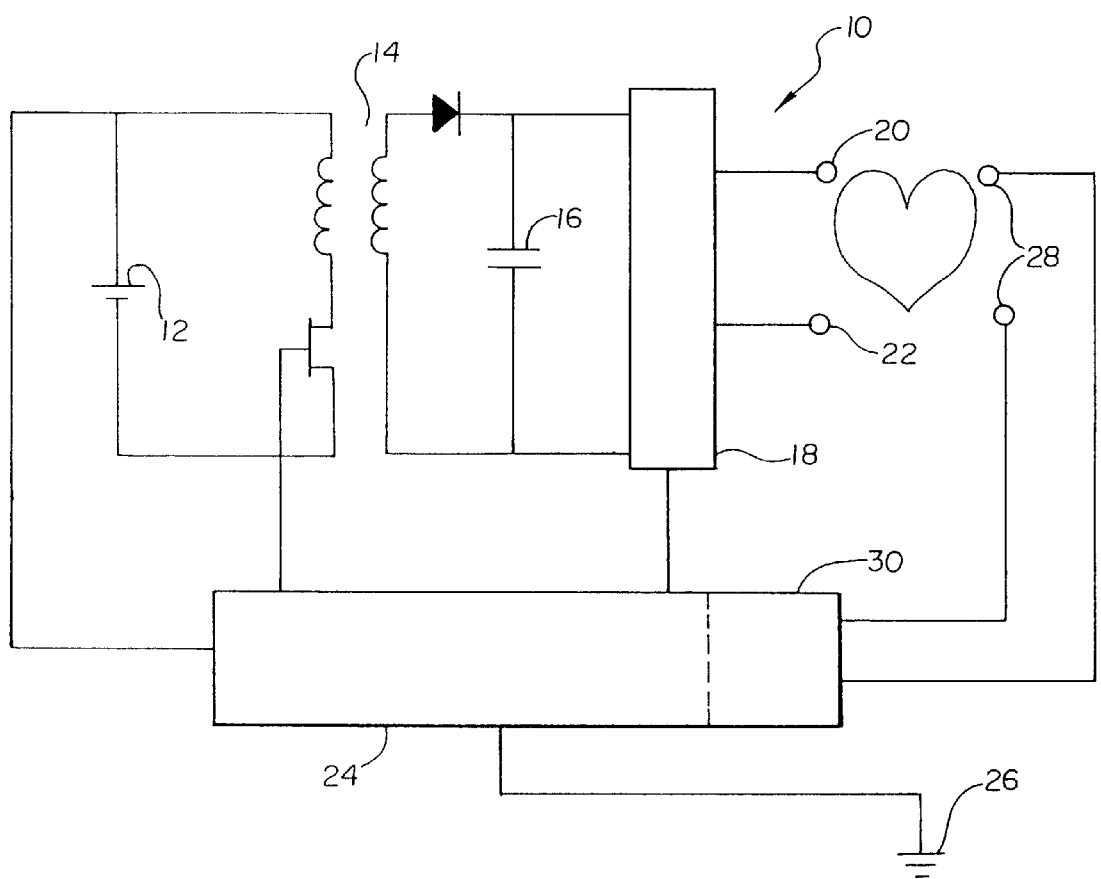
FIG. 1 is a simplified circuit diagram of an implantable cardioverter defibrillator (ICD) system.

Referring now to FIG. 1, a simplified circuit diagram of an implantable cardioverter defibrillator (ICD) system 10 in accordance with a preferred embodiment of the present invention is shown. ICD system 10 includes a battery system 12 connected to a high voltage transformer 14 for developing a high voltage across transformer 14 which is then applied to a capacitor system 16. The high voltage capacitor system 16 stores an electrical charge which is then selectively discharged through an output switching network 18 into electrodes 20, 22 as an electrical countershock for treating cardiac dysrhythmias. A control system 24, preferably a microcontroller or microprocessor with appropriate software and memory, is connected to the battery system 12, high voltage transformer 14 and output switching network 24 to control the charging and discharging of the electrical countershocks. Control system 18 preferably includes telecommunication circuitry 26 for communicating external to the patient in which ICD system 10 is implanted, as well as sensing electrodes 28 and sensing and detection circuitry 30 for detecting a cardiac dysrhythmia. It will be understood that the details and construction of ICD system 10 may be understood by reference to known ICD systems, such as described in U.S. Pat. No. 5,405,363 or ICD systems which are commercially available.

While the present invention is presented in terms of its application to a therapy delivery system which is described in terms of an ICD system 10, it should be understood that the present invention is applicable to any self-powered medical device which delivers a high voltage electrical countershock in response to the detection of a cardiac dysrhythmia, including cardioverters, atrial defibrillators and external defibrillators. Specifically, the preferred embodiment will be described in terms of an H-bridge output switching network 18 which is used to generate a conventional biphasic defibrillation waveform. It will be understood that the present invention is equally applicable to therapy delivery systems that deliver alternative countershock waveforms, such as multiphasic waveforms having more than two phases or steerable waveforms that are delivered between more than two electrodes. It will also be seen that the present invention is equally applicable to output switching networks having more than four legs on the H-bridge for controlling delivery of the countershock to more than two electrodes.

Figure 2:
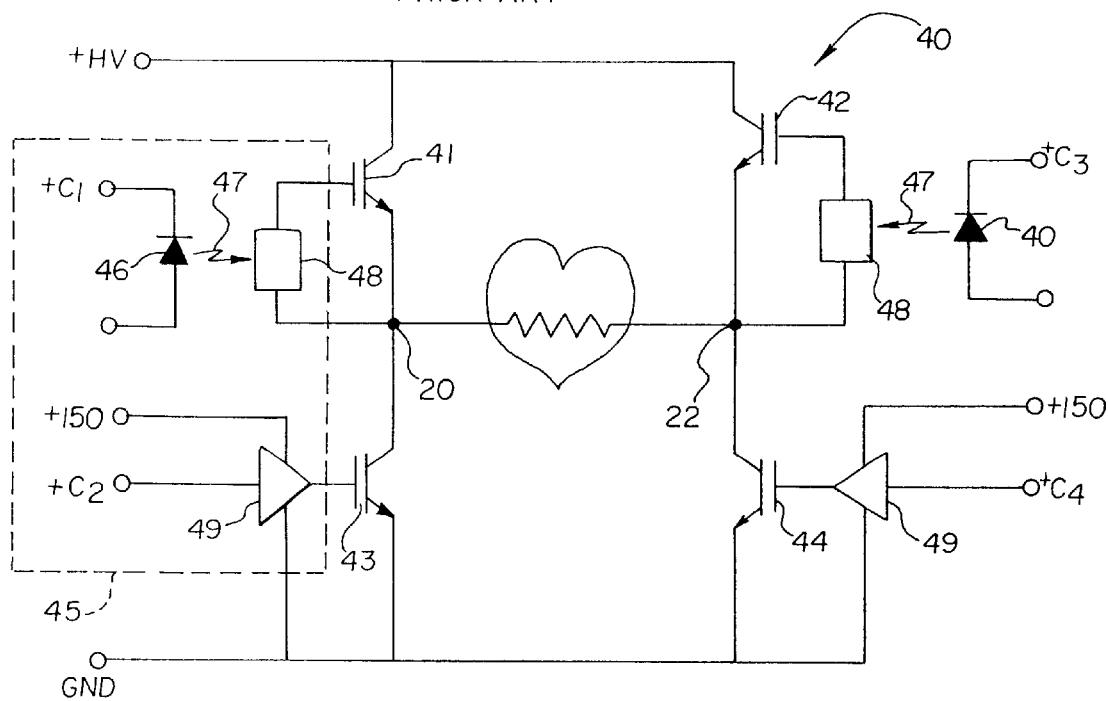
FIG. 2 is a simplified circuit diagram of the isolated output control circuitry for a prior art output switching network.

Referring now to FIG. 2, a simplified circuit diagram of the isolated output control circuitry 45 for a prior art output switching network 40 will be described. A conventional H-bridge switching circuit for switching network 40 is comprised of two high side switches 41, 42 connected between the high voltage side of the capacitor system 16 (+HV) and the two electrodes 20, 22, and two low side switches 43, 44 connected between the low voltage side of the capacitor system 16 (−GND) and the two electrodes 20, 22. The isolated output control circuitry 45 is comprised of a optoisolator having an LED 46 which emits a light signal 47 that is received by a photodiode or phototransistor 48. LED 46 is controlled by a control signal C1 supplied by control circuit 24. Photodiode 48 generates a current in response to the light signal 47 that provides the gate current to a gate input of an N-channel transistor switch 41. As long as light signal 47 is present, switch 41 is turned on. When light signal 47 is shut off by turning off control signal C1, then switch 41 will turn off as well. In contrast, the low side switch 43 is typically controlled by using an isolated amplifier 49 powered by an isolated low voltage power supply (+ISO). The isolated power supply is necessary for the low side switches 43, 44 because they are being used to control the current flow and operation of the H-bridge switch. A separate control signal C2 supplied by control circuit 24 is used to turn on amplifier 49, the output of which provides the gate current for switch 43. Although the switches 41, 42, 43 and 44 can be implemented using any number of different high voltage switches, the embodiment shown in FIG. 2 is represented using N-channel switches such as IGBT switches for switches 41, 42, 43 and 44.

Figure 3:
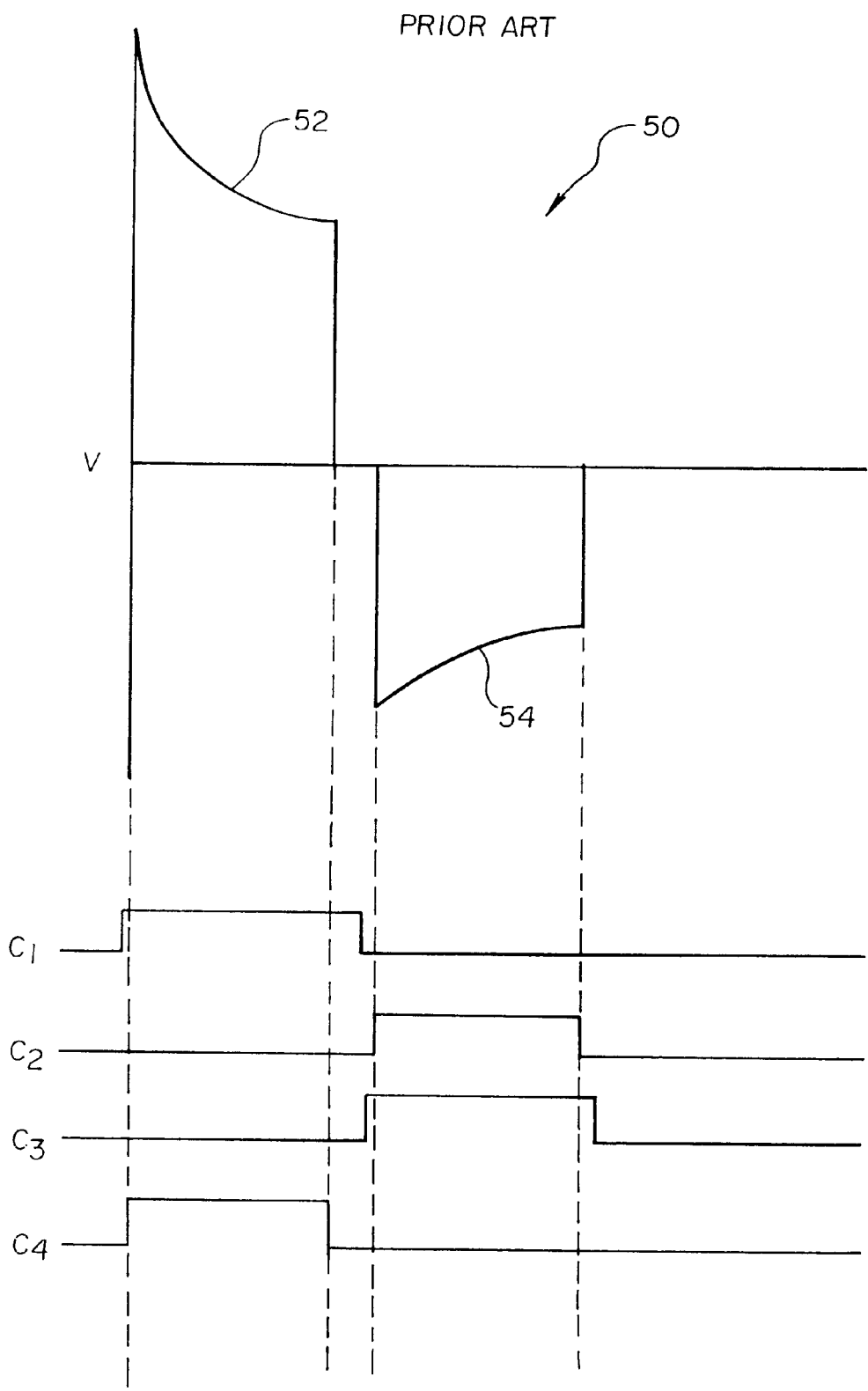
FIG. 3 is a graphical representation of a conventional biphasic waveform and the control signals as generated by the H-bridge output switching network of FIG. 2.

During delivery of a conventional biphasic waveform 50 as shown in FIG. 3, a first phase 52 is generated by having controller 24 first generate control signal C1 to turn on switch 41. Next, control signal C4 is applied to turn on switch 44, thereby causing current to flow through both switches 41 and 44 generating a positive going first phase 52 through electrodes 20, 22. After a given period of time which is typically measured by a fixed time interval, a specified percentage decay in the tilt of the waveform as measured by a drop in voltage output to a predetermined value, or some combination of these methods, controller 24 stops applying control signal C4, thereby turning off switch 44. This stops current flowing through the electrodes 20, 22 and through the legs of the H-bridge represented by switches 41 and 44. At this point, the first phase 52 has been truncated. After the current has stopped flowing through the high side leg of the H-bridge, control signal C1 is stopped in order to turn off switch 41. Now, controller 24 applies control signal C3 to turn on switch 42. Current begins to flow in the opposite directions through electrodes 22, 20 when control signal C2 is applied to turn on switch 43 to begin a second phase 54 of the biphasic waveform 50. After a second period of time which may be greater than, less than or equal to the first period of time for the first phase 52, the second phase 54 is truncated by stopping control signal C2 which turns off switch 43. Again, current stop flowing through electrodes 22, 20 and through the legs of the H-bridge represented by switches 42, 43. Finally, control signal C3 is stopped, shutting off switch 42 and completing the delivery of biphasic waveform 50. For a more detailed description of the timing for conventional operation of a photodiode controlled H-bridge switching network, reference is made to U.S. Pat. No. 5,626,619, Cols. 11–12.

While the prior art isolated output control circuitry 45 works to create a biphasic waveform 50, one disadvantage of this circuit is the lag time in turning on switches 41, 42 due to the limited amount of current which is available from photodiode 48. A limited current source from the photodiode or phototransistor 48 was not a problem when the high side switches 41, 42 were SCR switches because very little voltage or current was required to turn the SCR switches on. The problem with SCR switches, however, was an inability to quickly or easily turn these switches off. If N-channel switches, such as an IGBT switch, are used in place of the SCR switch to overcome this problem, then the amount of current and voltage supplied by photodiode or phototransistor 48 ends up being a limitation in terms of how fast the high side switches 41, 42 can be turned on and off, which in turn can lead to the problems of hot switching as previously discussed. The prior art has overcome the problem of hot switching to date by using the low side switches 43, 44 to control the flow of current through the H-bridge, thereby preventing any hot switching of high side switches 41, 42.

In an attempt to solve the problem of limited current availability, other prior art devices have used a photodiode array consisting of multiple photodiode elements arranged in series or parallel to generate the gate current for switch 41. In addition, multiple LEDs 46 may also be used to generate a stronger light signal 47. Unfortunately, these solutions do not address the separate problem of how to actively shut off high side switches 41, 42 during hot switching.

Figure 4:
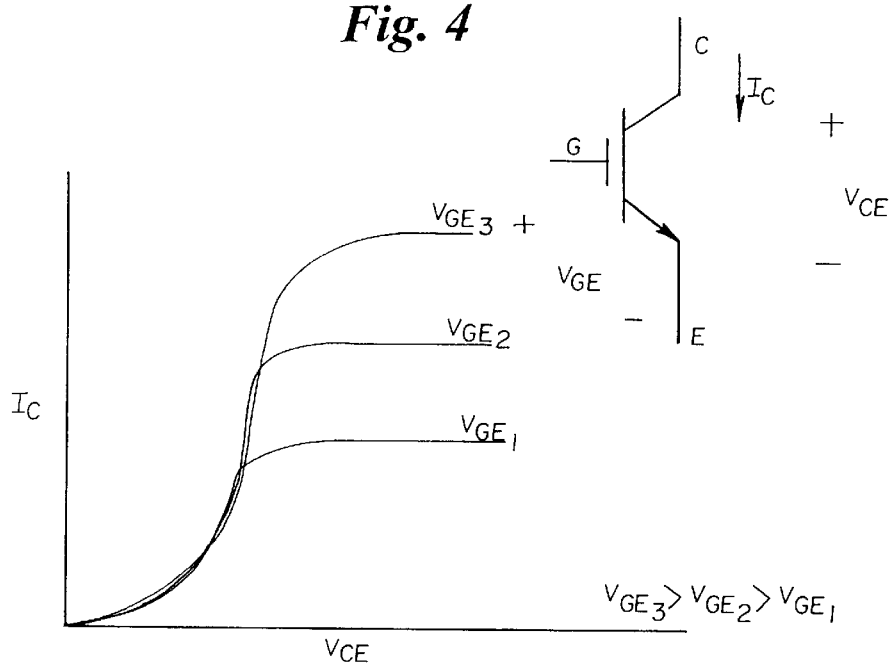
FIG. 4 is a graphical representation of the voltage and current across the gate to emitter of an N-channel IGBT high power switch.

The problems of hot switching of the IGBT high side switches 41, 42 can best be understood by reference to FIG. 4 which shows a graph of the relationship between the current and voltage across the collector to emitter of a high power IGBT switch. It can be seen that if the IGBT switch operates along the vertical portion of the curve, then the switch can handle ever increasing amounts of current without dissipating additional power through the switch because the power dissipated across the switch is determined by $P=V_{CE}*I_C$. It also can be seen that the larger the gate voltage, the larger the vertical portion of the curve. For an IGBT high power switch, the voltage between the gate and emitter is effectively determined by the amount of current supplied to the gate. This gate current charges an equivalent capacitance between the gate and emitter that establishes the voltage between the gate and emitter.

Instead of relying on low side switching to control the operation of the H-bridge, the present invention addresses the problem of hot switching of an N-channel high side switch by increasing the current available to the gate of the high side switch, thereby increasing the gate to emitter voltage. An increase in the gate to source voltage decreases the transition time of the N-channel switch during which the vast majority of the energy dissipation across the switch occurs. As a result, the present invention is able to address the problem of hot switching of the high side switches directly, without the need to rely on control of the H-bridge by the low side switches. Instead of relying on the output of an optoisolator device to provide both the isolated supply and the gate drive current as has been done in the prior art, the present invention separates the isolated supply from the gate drive current and amplifies the gate drive current using the separated isolated supply to increase the voltage across the gate to emitter of the N-channel high side switch. This is a significant advantage, both in terms of switching speed and number of times that the H-bridge switch can be cycled, as well as in terms of the safety afforded by the present invention. Specifically, because the high side switches are being used to control the operation of the H-bridge circuitry, a short circuit in the output across the low side switches does not result in a situation where an unintended discharge would continue due to an inability to turn off current flowing from the high side legs of the H-bridge.

Figure 5:
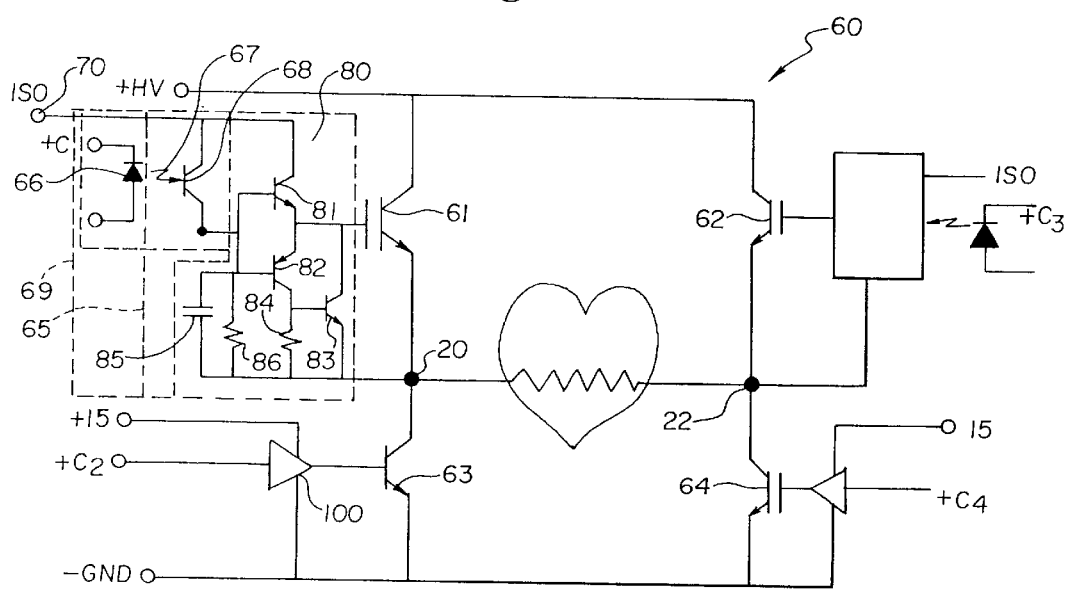
FIG. 5 is a simplified circuit diagram of the isolated output control circuitry of a preferred embodiment of the present invention.

Referring now to FIG. 5, a preferred embodiment of the isolated output control circuitry 65 for the output switching network 60 of the present invention will be described. As with the prior art network 40, the output switching network 60 is shown in this embodiment to consist of four high voltage N-channel switches, two high side switches 61, 62 and two low side switches 63, 64. Preferably, the switches 61, 62, 63 and 64 are IGBT switches, although N-channel MOSFET switches or the like could be used. It would be possible to implement portions of the present invention with high power P-channel switches, should such devices become available in the future. It will be understood that additional legs of the H-bridge circuitry can be added, for example, to support a switchable CAN electrode in addition to the +DEFIB and −DEFIB electrodes represented by electrodes 20, 22. As with the prior art output control circuitry 45, the preferred embodiment of the isolated output control circuitry 65 of the present invention also utilizes control signals C1–C4 which are generated by controller 24.

Figure 6:
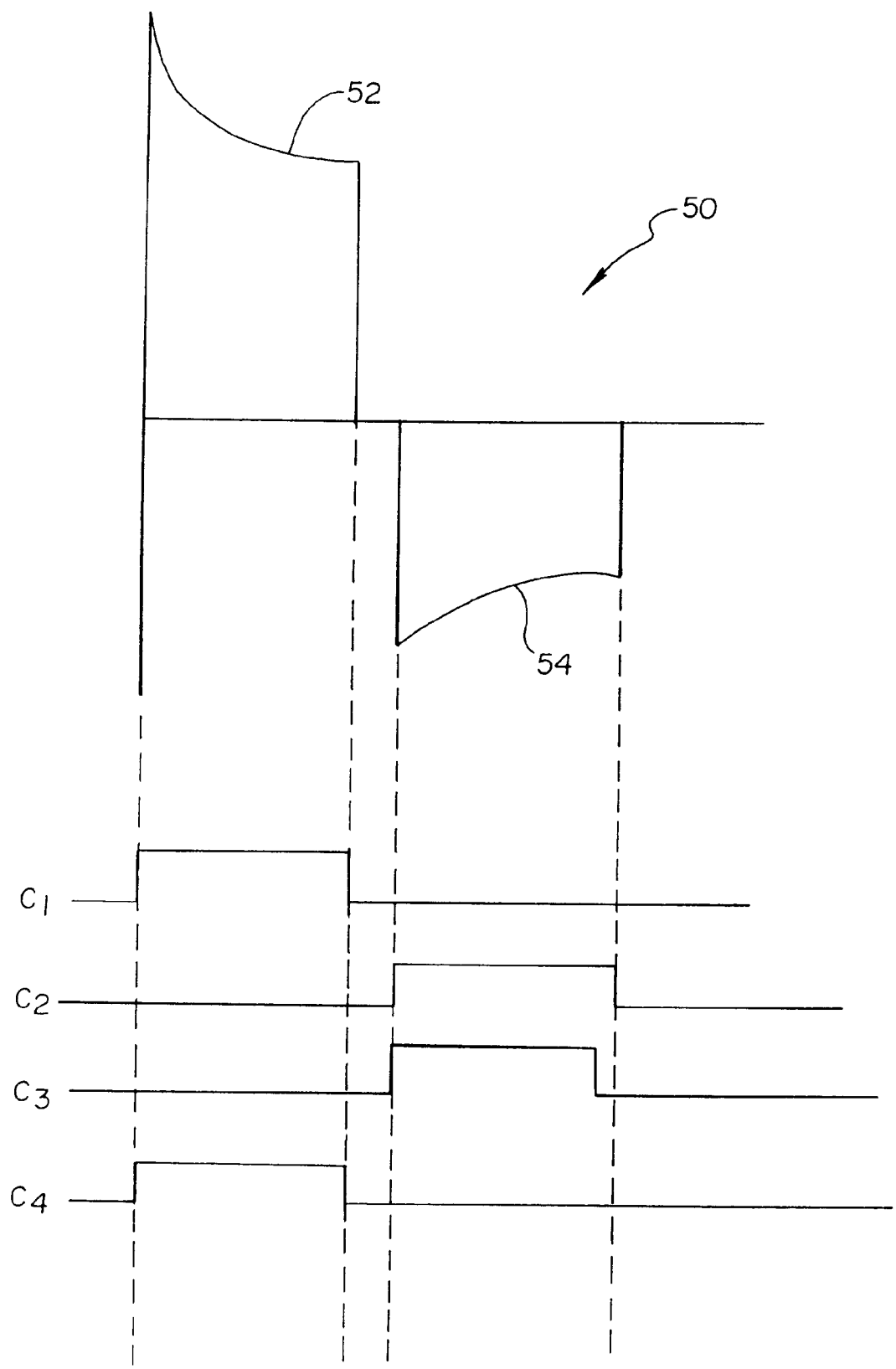
FIG. 6 is a graphical representation of a conventional biphasic waveform and the control signals as generated by the H-bridge output switching network of FIG. 5.

Unlike the prior art, isolated output control circuitry 65 is able to control the operation of the H-bridge circuit by using the high side switches 61, 62 instead of relying on the low side switches 63, 64 to determine when current does or does not flow through the legs of the output switching network 60. The result as shown in FIG. 6 is that control signals C1 and C3 are turned on and off at the same time as the biphasic waveform 50. It should be understood that control signals C2 and C4 may be turned on prior to and after control signals C1 and C3 to avoid hot switching of the low side switches 63, 64, or control signals C2 and C4 may be applied simultaneously with control signals C1 and C3 to enable hot switching of all four switches 61, 62, 63 and 64. In a preferred embodiment, control signals C2 and C4 are applied about 100 microseconds after control signals C1 and C3.

To accomplish high side control of the H-bridge and hot switching of the high side switches 61, 62, the present invention relies primarily on two novel features, an isolated high voltage supply 70 and an amplifier section 80 that are integrated with the optocoupler 69 to form the isolated output control circuitry 65. The optocoupler 69 preferably consists of a photodiode 66 that emits a light signal 67 which is received by the base of a phototransistor 68. Preferably, optocoupler 69 is an MC022 or any equivalent optocoupler. It will be understood that while it is preferable to utilize a phototransistor 68 in accordance with the present invention, the present invention would also be applicable to isolated output control circuits which utilize a photovoltaic element or a photovoltaic array to receive the light signal 67 and which have an output that is coupled to the base of a transistor that is powered by the isolated high voltage supply 70.

Figure 8:
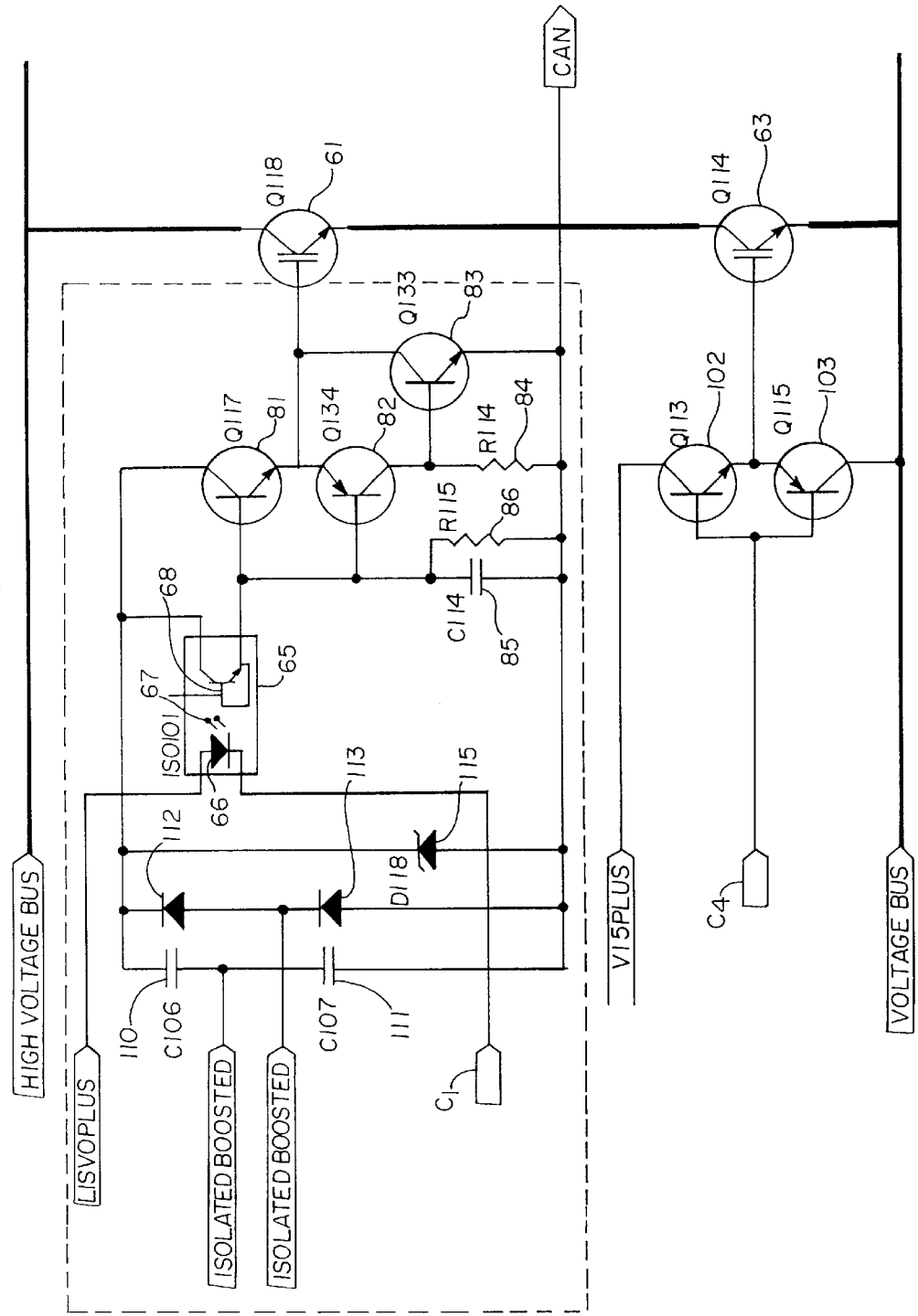
FIG. 8 is a detailed circuit diagram of the isolated output control circuitry of FIG. 5.

The purpose of the amplifier section 80 is to increase the current supplied to the base of the high side switches 61, 62, thereby allowing these switches to be turned on much faster and avoid the heat dissipation which occurs during relatively slow hot switching of these switches. As shown in FIGS. 5 and 8, a pair of transistors a first NPN transistor 81 and a PNP transistor 82 are arranged in a totem pole configuration between the output of optoisolator 69 and the gate of switch 61. In addition, amplifier section 80 preferably includes an amplified turn-off circuitry consisting of a second NPN transistor 83 and a resistor 84 connected between the gate of switch 61 and the common for electrode 20 and the emitter of switch 61, as well as a capacitor 85 and resistor 86 connected between the gate of transistor 82 and the common for electrode 20 and the emitter of switch 61. Because amplifier section 80 is powered by isolated supply 70, there is a relatively unlimited and immediate supply of current for powering the gate of switch 61 as compared to the prior art circuitry where the current for the base of switch 41 had to be supplied in its entirety by the output of the photovoltaic array. Moreover, the beta gain of the phototransistor 68 is multiplied by the beta gain of the first NPN transistor 81 to provide a significantly increased instantaneous current at the gate of switch 61. Similarly, the beta gain of PNP transistor 82 and second NPN transistor 83 provide a significantly increased current that can pass through resistor 84 to shut off the gate current to switch 61.

One of the advantages of this arrangement is that switches 61 and 62 are preferably IGBT switches such as 1XGD1687 or any equivalent IGBT switch, rather than the conventional SCR switches which are used for the high side switches of the H-bridge. It should be noted that, unlike conventional SCR switches, the IGBT switches may have a greater ESR leading to a somewhat larger voltage drop across the switch as it is operated. This can be offset by nominally increasing the voltage at which the H-bridge circuitry operates such that the delivered voltage across electrodes 20, 22 is the same as would have been delivered from a conventional H-bridge switch.

In this embodiment, the present invention does not have the limitation on the number of times that the H-bridge circuit can be cycled. As a result, it is possible for the output switching network 60 of the present invention to be cycled numerous time during a conventional discharge time period of 1–10 ms without incurring the problems of overheating which are incumbent in the prior art design. This in turn makes available the possibility of waveforms having more than two phases being delivered in the same time period as a conventional biphasic waveform.

Figure 7:
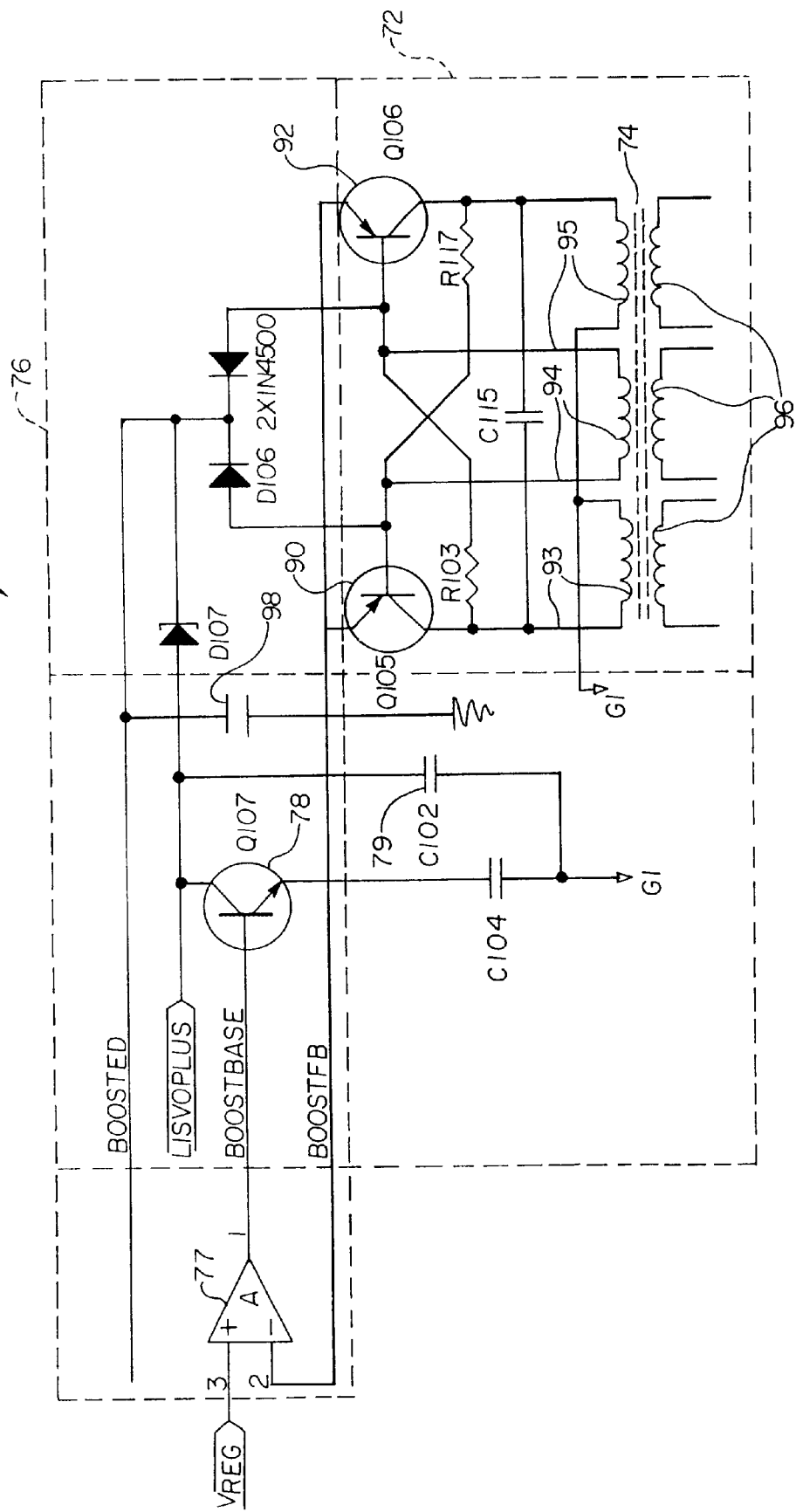
FIG. 7 is a detailed circuit diagram of a preferred embodiment of the isolated power supply of FIG. 5.

Referring now to FIG. 7, the preferred embodiment of the isolated supply 70 will be described. In the preferred embodiment in which the high side switches 61, 62 are high power N-channel IGBT transistors, it is necessary to have the isolated supply 70 source a voltage of about 15 V at a nominal current delivery of approximately 40 amps. In the preferred embodiment, isolated supply 70 is comprised of a dc to dc converter 72 that includes a transformer 74, preferably a multiple winding ferrite toroid transformer. Because of the nature of the preferred implementation of converter 72 and transformer 74, a booster circuit 76 is also provided that generates a current boosted supply for the control circuitry 24 and other critical components within the ICD 10 during charging and discharging of the capacitors 16 when converter 72 is operating.

In the preferred embodiment, the converter 72 is a dc to dc converter in the form of a Royer relaxation oscillator (multivibrator). A comparator 77 within the booster circuit 76 controls the power to the converter oscillator 72 via transistor 78 such that the voltage supplied to converter oscillator 72 will be regulated by $V_{REG}$, which in turn can be digitally controlled by control circuitry 24. The battery 12 for an implantable defibrillator typically is comprised of one or two +3 V lithium silver vanadium oxide (SVO) battery cells which is connected to the isolated supply 70 at LIS-VOPLUS. The supply voltage from battery 12 is supported within the isolated power supply 70 by a small capacitor 79 that is nominally about 2 $\mu F$. The multivibrator oscillator converter 72 oscillates by virtue of an existing positive feedback sent to the bases of transistors 90, 92 through the middle winding 94 of transformer 74. When the oscillation starts, transistors 90, 92 are each in a 50% duty cycle alternating between conducting and non-conducting states, thus impressing the supply voltage on their respective collector windings 93, 95. The secondary side windings 96 of transformer 74 provide an AC peak-to-peak voltage of between +15 V to +20 V as an isolated voltage supply for isolated control circuitry 65 as shown in FIG. 8. The booster 74 taps into the outputs of converter oscillator 72 at the outputs of transistors 90, 92 and provides a boosted supply of about 4.5 V to control circuitry 24 at BOOSTED which is also protected by a capacitor 98 that is similar to capacitor 79. A feedback line (BOOSTFB) is compared by comparator 77 with the VREG signal to alter the output of the converter 72 and the output of the booster 74 if desired.

Referring now to FIG. 8, the output of the secondary windings of transformer 72 is connected to the isolated output control circuitry 65 between a pair of input capacitors 110, 111 and a pair of diodes 112 113 which together form a rectifying doubler which generates a rectified DC voltage that is generally clamped between +15 to +20 V across a zener diode 115. When the photodiode 66 for optoisolator 69 is pulled low by the control signal C1, the totem pole transistor 81 receives a base current from the output of phototransistor 68 that is sufficient to turn it on, thereby connecting the base (gate) of switch 61 to the DC voltage from the isolated supply 70. The IGBT switch 61 subsequently turns on delivering the high voltage present at +HV to the electrode 20.

To allow current to flow through both legs of the H-bridge switch, the low side switch 64 is turned on prior to or at the same time as switch 61 is turned on. In the preferred embodiment, the low side switches 63, 64 do not require an isolated power supply because their gate drivers 100 can be connected to the −GND as a common. In the preferred embodiment, each gate driver 100 is comprised of a totem pole push-pull pair of transistors 102, 103 that are powered by a boosted voltage signal that is generated for other purposes by control circuitry 24. In the preferred embodiment, this boosted voltage signal is generated for pacing purposes and is also used to provide boosted non-isolated power to the low side control circuitry. Alternatively, isolated power supply 70 could be used for the low side switches 63, 64 although this may involve increasing the capacity of transformer 72. The control signals C4 is supplied to the base of transistor 102 which in turn allows the necessary +15 V signal to be applied to the base of IGBT switches 64, thereby turning this switch on.

In order to turn the high side switch 61 off, the input photodiode 66 is disconnected from its current source by withdrawing control signal C1. In the preferred embodiment, this is accomplished by forcing a high impedance onto control signal C1. As a result, the base of transistor 81 is turned off and transistors 82 and 83 are quickly turned on, thereby forcing IGBT switch 61 off by effectively connecting the base of switch 61 to its emitter. Transistor 83 is used as an amplified turn off of switch 61 to enhance the switching speed by using the gain of transistor 83 to increase the gain for the turn off process. In this embodiment, resistor 84 is approximately 470 K ohms to facilitate the speed at which the turn off process can be performed.

Having thus described the preferred embodiments of the present invention, those skilled in the art will readily appreciate the many other embodiments which can be employed within the scope of the claims provided below.

We claim:

1. A self-powered defibrillator for delivering a high voltage electrical countershock through a plurality of electrodes, the defibrillator comprising:

a low voltage battery system;

a high voltage capacitor system;

a high voltage transformer having a primary side operably connected to the battery system and a secondary side operably connected to the capacitor system;

an output switching network operably connected between the capacitor system and the plurality of electrodes;

isolated output control circuitry operably connected to the output switching network, the isolated output control circuitry including an isolated power supply, at least one optoisolator device having an input and an output, and at least one amplifier circuit powered by the isolated power supply and having an input connected to the output of the optoisolator device and an output connected to the output switching network and having a beta gain that increases the instantaneous current supplied to the output switching network; and control circuitry operably connected to the battery system, the high voltage transformer and the input of the at least one optoisolator device of the isolated output control circuitry to control the charging and discharging of the electrical countershock.

2. The self-powered defibrillator of claim 1 wherein the output switching circuitry comprises at least two low side switches operably connected to a ground side of the secondary side of the transformer and at least two high side switches operably connected to a high voltage side of the secondary side of the transformer and wherein the isolated output control circuitry includes an optoisolator device and an associated amplifier circuit for at least each high side switch, the output of each amplifier circuit being connected to a gate of an associated one of the switches.

3. The self-powered defibrillator of claim 1 wherein the isolated output control circuitry further comprises an amplified turn-off circuit operably connected to the output of the amplifier.

4. The self-powered defibrillator of claim 1 wherein the optoisolator device is a phototransistor having a base as the input and an emitter as the output.

5. The self-powered defibrillator of claim 1 wherein the amplifier circuit comprises:

a first NPN transistor having a collector connected to the isolated power supply, a base connected to the output of the phototransistor and an emitter connected to a gate input for the output switching network;

a second NPN transistor having a collector connected to the gate input for the output switching network, a base and an emitter connected to an emitter output for the output switching network;

a PNP transistor having a emitter connected to the gate input for the output switching network, a base connected to the output of the phototransistor and an collector connected to the base for the second NPN transistor;

an RC circuit connected between the base of the PNP transistor and the emitter output for the output switching network; and a resistor connected between the base of the second NPN transistor and the emitter output for the output switching network.

6. The self-powered defibrillator of claim 1 wherein the output switching network includes at least two high power N-channel transistor switches.

7. A self-powered defibrillator for delivering a high voltage electrical countershock through a plurality of electrodes, the defibrillator comprising:

a low voltage battery system;

a high voltage capacitor system;

a high voltage transformer having a primary side operably connected to the battery system and a secondary side operably connected to the capacitor system;

an output switching network operably connected between the capacitor system and the plurality of electrodes, the output switching circuitry comprises at least two low side switches operably connected to a ground side of the secondary side of the transformer and at least two high side switches operably connected to a high voltage side of the secondary side of the transformer;

isolated output control circuitry operably connected to the output switching network, the isolated output control circuitry including an isolated power supply and for at least each high side switch an optoisolator device having an input and an output and an amplifier circuit powered by the isolated power supply and having an input connected to the output of the optoisolator device and an output connected to a gate input of the high side switch and having a beta gain that increases the instantaneous current supplied to the gate input of the high side switch; and control circuitry operably connected to the battery system, the high voltage transformer and to the input of at least each optoisolator device of the isolated output control circuitry to control the charging and discharging of the electrical countershock.

8. The self-powered defibrillator of claim 7 wherein the isolated output control circuitry further comprises for each low side switch an amplifier powered by a non-isolated power supply and having an input and an output connected to a gate input of the low side switch.

9. The self-powered defibrillator of claim 8 wherein the control circuitry controls the output switching network by first sending a control signal for the low side switches and then sending a control signal for the high side switches so as to provide for high side control of the output switching network.

10. The self-powered defibrillator of claim 7 wherein the isolated output control circuitry further comprises an amplified turn-off circuit operably connected to the output of the amplifier.

11. The self-powered defibrillator of claim 7 wherein the optoisolator device is a phototransistor having a base as the input and an emitter as the output.

12. A self-powered defibrillator for delivering a high voltage electrical countershock through a plurality of electrodes, the defibrillator comprising:

a low voltage battery system;

a high voltage capacitor system;

a high voltage transformer having a primary side operably connected to the battery system and a secondary side operably connected to the capacitor system;

an output switching network operably connected between the capacitor system and the plurality of electrodes, the output switching circuitry comprises at least two low side switches operably connected to a ground side of the secondary side of the transformer and at least two high side switches operably connected to a high voltage side of the secondary side of the transformer; and control means operably connected to the battery system, the high voltage transformer and output switching network to control the charging and discharging of the electrical countershock by first generating a control signal for the low side switches and then generating a control signal for the high side switches so as to provide for high side control of the output switching network.

13. A self-powered defibrillator for delivering a high voltage electrical countershock through a plurality of electrodes, the defibrillator comprising:

a low voltage battery system;

a high voltage capacitor system;

a high voltage transformer having a primary side operably connected to the battery system and a secondary side operably connected to the capacitor system;

an output switching network operably connected between the capacitor system and the plurality of electrodes;

an isolated power supply that provides an isolated output and a boosted output;

isolated output control circuitry operably connected to the output switching network and the isolated output; and control circuitry operably connected to the battery system, the high voltage transformer and the isolated output control circuitry to control the charging and discharging of the electrical countershock, the control circuitry further being operably connected to the boosted output of the isolated power supply at least during charging of the capacitor system to insure an adequate supply of power to the control circuitry during charging of the capacitor system.

* * * * *